(12) United States Patent  
Campbell et al.

(10) Patent No.: US 6,370,426 B1  
(45) Date of Patent: Apr. 9, 2002

(54) METHOD AND APPARATUS FOR MEASURING RELATIVE HYDRATION OF A SUBSTRATE

(75) Inventors: Michael J. E. Campbell, Meredith; Michael L. Gallant, Gilford; Dennis D. Giguere, Bow; Thomas B. Horgan; Steven W. Nickson, both of Derry, all of NH (US); Richard W. Sheppe, Jr., Post Mills, VT (US)

(73) Assignee: Nova Technology Corporation, Portsmouth, NH (US)

(*) Notice: Subject to any disclaimer, the term of this patent is extended or adjusted under 35 U.S.C. 154(b) by 0 days.

(21) Appl. No.: 09/552,972

(22) Filed: Apr. 20, 2000

Related U.S. Application Data (60) Provisional application No. 60/130,080, filed on Apr. 20, 1999.

(51) Int. Cl.[7] ................................. A61B 5/05
(52) U.S. Cl. ................. 600/547; 600/306; 324/696
(58) Field of Search ........................ 600/306, 307, 600/547, 554, 557; 324/664, 688, 689, 692, 694, 696

(56) References Cited

U.S. PATENT DOCUMENTS

| 4,096,852 | A | * | 6/1978 | Adams ........................ 182/2 |
|---|---|---|---|---|
| 4,697,599 | A | * | 10/1987 | Woodley et al. ............ 600/547 |
| 4,860,753 | A | | 8/1989 | Amerena ..................... 600/306 |
| 4,966,158 | A | * | 10/1990 | Honma et al. ............... 600/547 |
| 5,001,436 | A | * | 3/1991 | Scot et al. ................... 324/689 |
| 5,240,010 | A | * | 8/1993 | Weinmann ................... 600/547 |
| 5,353,802 | A | * | 10/1994 | Ollmar ........................ 600/547 |
| 5,588,440 | A | | 12/1996 | Cowie ......................... 600/547 |
| 5,738,107 | A | * | 4/1998 | Martinsen et al. .......... 600/547 |
| 5,755,672 | A | * | 5/1998 | Arai et al. ................... 600/547 |
| 5,897,505 | A | | 4/1999 | Feinberg et al. ............ 600/547 |
| 5,961,471 | A | * | 10/1999 | Nickson ....................... 600/546 |

FOREIGN PATENT DOCUMENTS

| DE | 2912349 A | 10/1980 |
|---|---|---|
| DE | 29514982 | 7/1996 |

* cited by examiner

Primary Examiner—Kevin Shaver  
Assistant Examiner—Charles Marmor, II  
(74) Attorney, Agent, or Firm—George A. Herbster (57) ABSTRACT

A method and apparatus for measuring relative hydration of a substrate. Measurements of the electrical characteristics of the substrate and the force applied to and the temperature of the substrate during the measurement provide inputs for determining such relative hydration of the substrate.

24 Claims, 9 Drawing Sheets

METHOD AND APPARATUS FOR MEASURING RELATIVE HYDRATION OF A SUBSTRATE

CROSS-REFERENCE TO PROVISIONAL APPLICATION

This application is based upon Provisional Application No. 60/130,080 filed Apr. 20, 1999 by Michael J. E. Campbell et al. for a Method and Apparatus for Measuring Biophysical Characteristics of the Skin.

BACKGROUND OF THE INVENTION

1. Field of the Invention

This invention generally relates to devices for measuring relative hydration of a substrate, such as hydration of the human skin or physical substrate materials.

2. Description of Related Art

There is a growing interest in measuring the relative hydration of a substrate. For example, such measurements on human skin provides information about wound healing. Measurements on hydration through films, such as bandages and tapes, can indicate the efficacy of certain compositions of such bandages or tapes in connection with the healing process.

A number of devices exist for measuring relative hydration of human skin by measuring the water content of the skin typically by measuring skin impedance. For example, U.S. Pat. No. 5,961,471 issued Oct. 5, 1999 by Steven W. Nickson for a probe for a biophysical skin measurement device discloses one such device for measuring relative skin hydration that has received wide acceptance.

It has been recognized that variations in the force at which such a probe is applied to the skin can affect the measured impedance. For example, U.S. Pat. No. 5,001,436 (1991) to Scott et al. discloses a skin impedance measuring device that recognizes a necessity for some method of controlling the pressure applied. Scott et al. monitor the force applied by the probe and trigger the measurement when an acceptable force exists. U.S. Pat. No. 5,588,440 (1996) to Cowie discloses a system for measuring skin temperature and measuring force. However, the force measurement merely provides an indication of the force as a guide for helping the user control the force at which measurements are taken. In both disclosures it becomes incumbent on the operator to control the force manually in order to obtain sustained measurements.

Notwithstanding these attempts to compensate for temperature and force in skin moisture measurement devices, there is still a requirement for a relative hydration measuring system that will automatically compensate for the effects of force and temperature variations during the measurement process.

SUMMARY

Therefore it is an object of this invention to provide a relative hydration measuring device and method that can compensate for the force applied by a measurement probe.

Another object of this invention is to provide a relative hydration measuring device and method that can compensate for the temperature of the substrate being tested.

Yet another object of this invention is to provide a relative hydration measuring system for human skin that automatically produces a moisture indication that can be compensated for probe force and skin temperature during the measurement.

In accordance this invention, relative substrate hydration is obtained by measuring the electrical characteristics of the substrate between electrodes contacting the substrate and by measuring concurrently an environmental factor. These measurements provide the basis for obtaining a value of substrate impedance between the electrodes that indicates relative hydration.

In accordance with another aspect of this invention, a system for measuring the relative hydration of a substrate comprises a probe having first and second electrodes for contacting the substrate. An electrical impedance measurement circuit periodically generates a value representing the impedance of the substrate between the first and second electrodes. An environmental factor measurement circuit periodically generates a value representing an environmental factor associated with the impedance measurement. A calculator may respond to the impedance and environmental factors signals to produce an indication of relative hydration.

In accordance with yet another aspect of this invention, a system for measuring the relative hydration of a substrate includes a measurement probe and a data processing system. The measurement probe comprises an elongated probe housing and a sensor body mounted at one end of the probe housing with first and second concentric electrodes for contacting the substrate at a site for which a relative hydration measurement is desired. An electrical impedance measurement circuit in the probe housing generates an impedance signal including information about the capacitive reactance between the first and second electrodes. A force sensor in the probe housing generates a signal representing the force exerted by one of the electrodes on the substrate. A signal processor in the probe housing polls the electrical impedance measurement circuit and the force sensor thereby to generate processed impedance and force measurement signals. A connector at the other end of the probe housing enables communications between the data processing system and the signal processor.

In accordance with still another aspect of this invention, a system for measuring relative hydration of a substrate includes a measurement probe and a data processing system. The measurement probe comprises an elongated probe housing and a sensor body mounted at one end of the probe housing with first and second concentric electrodes for contacting the substrate at a site for which a measurement of relative hydration is desired. An electrical impedance measurement circuit in the probe housing generates an impedance signal representing the impedance of the substrate between the first and second electrodes. A temperature sensor in the probe housing generates a signal representing the temperature of the skin contacting the electrodes. A signal processor in the probe housing polls the impedance measurement circuit and the temperature sensor thereby to generate processed impedance and temperature measurement signals. A connector at the other end of the probe housing enables communications between the data processing system and the signal processor.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
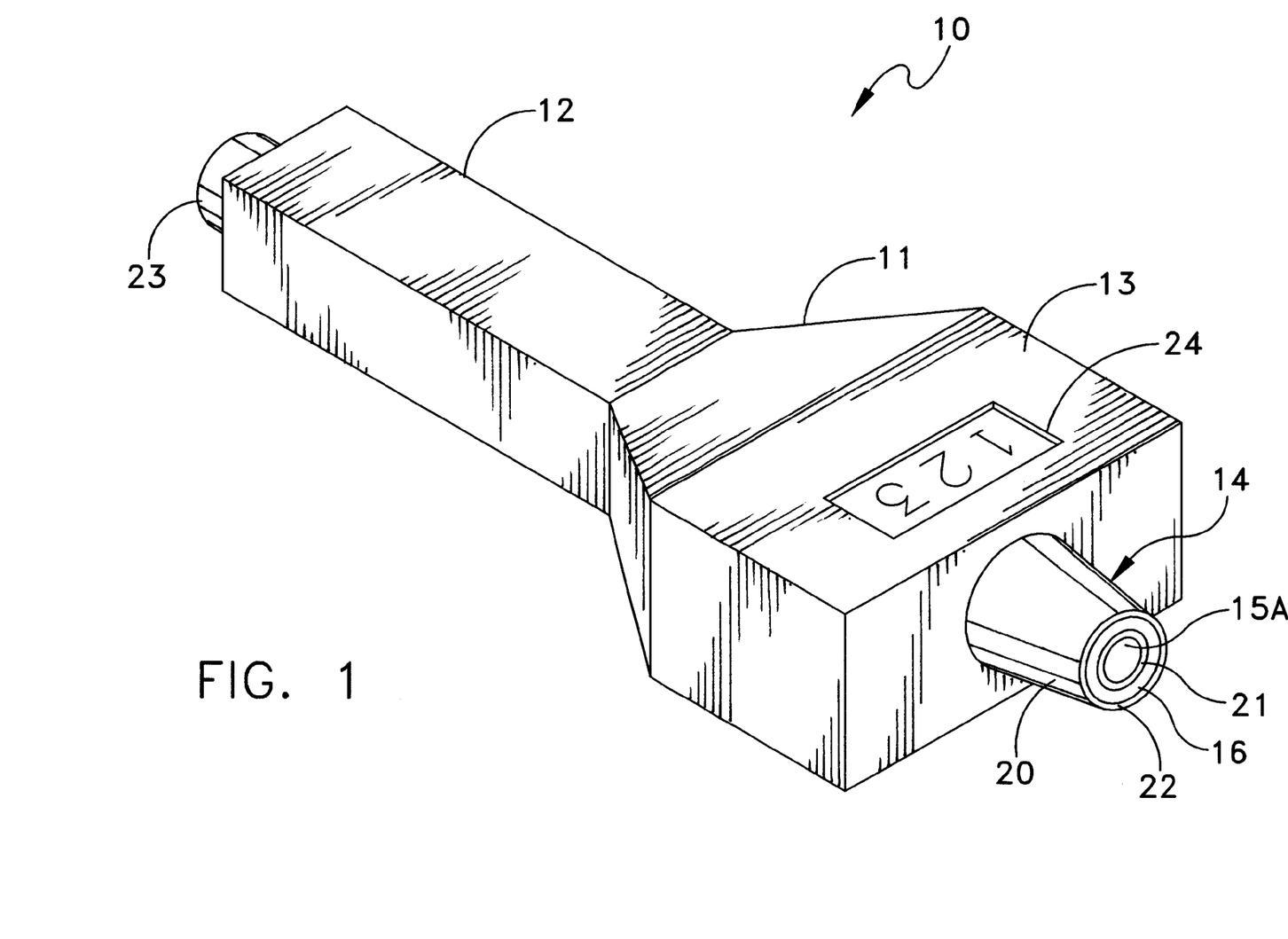
FIG. 1 depicts a measurement sensor constructed in accordance with this invention.

FIG. 1 depicts one embodiment of a probe 10 that includes a housing 11 forming a handle 12 and a probe head 13. In this particular embodiment the handle 12 and probe head 13 are in different planes to facilitate operator use in making measurements on human skin or other substrates, such as bandages and tapes. In the following discussion, "substrate" is intended to cover both skin and such other substrates.

The probe head 13 carries a sensor head 14 that has a number of sensing elements including a centrally disposed temperature sensor 15 and first and second spaced electrodes. The temperature sensor 15 that could be based upon thermistor or thermocouple sensors, could include an electrically isolated conductive housing or can 15A that can act as an inner electrode independently of the operation of the temperature sensor 15. This electrode 15A and a spaced outer, concentric electrode 16 act as impedance moisture electrodes. A sensor housing 20 contains these elements as well as an insulator 21 disposed between the temperature sensor, acting as the inner electrode 15A, and outer electrode 16 and another insulator 22 disposed about the outer electrode 16. Thus the electrodes 15A and 16 are insulated from each other and from the temperature sensor 15. A connection 23 at the end of the handle 12 constitutes an interface for attaching the probe 10 to a data processing system thereby to enable data to be processed remotely from the probe 10 and to allow a single data processing system to accept different probes. If the probe 10 contains an LCD or other display 24 or other electronically driven readout, the signals for such a display 24 could be generated internally of the probe 10 or coupled to the probe 10 through the connection 23. generated internally of the probe 10 or coupled to the probe 10 through the connection 23.

Figure 2:
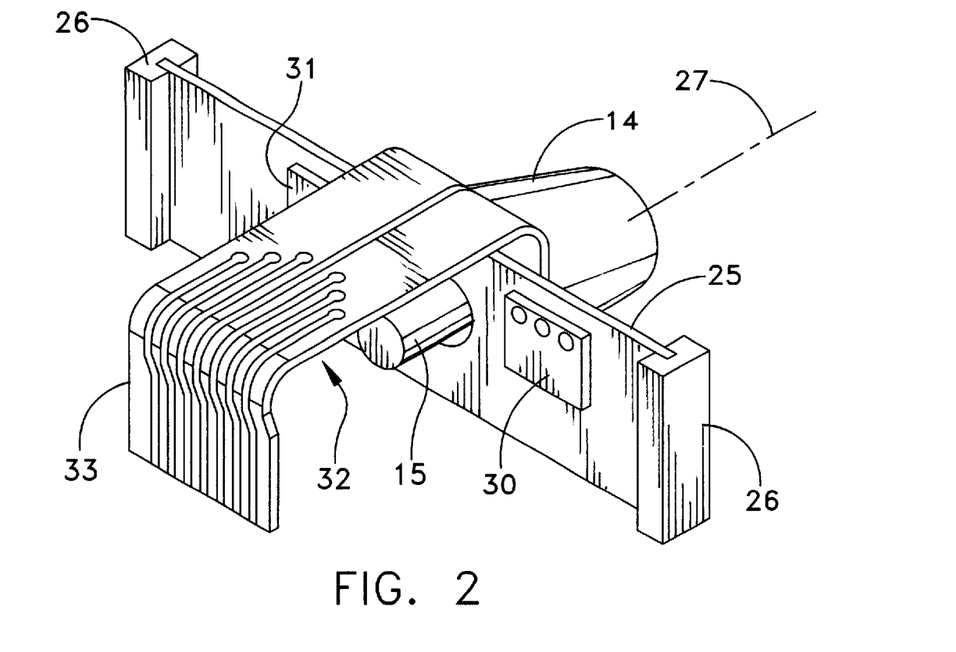
FIG. 2 is a view of a portion of the sensor shown in FIG. 1.
Figure 3:
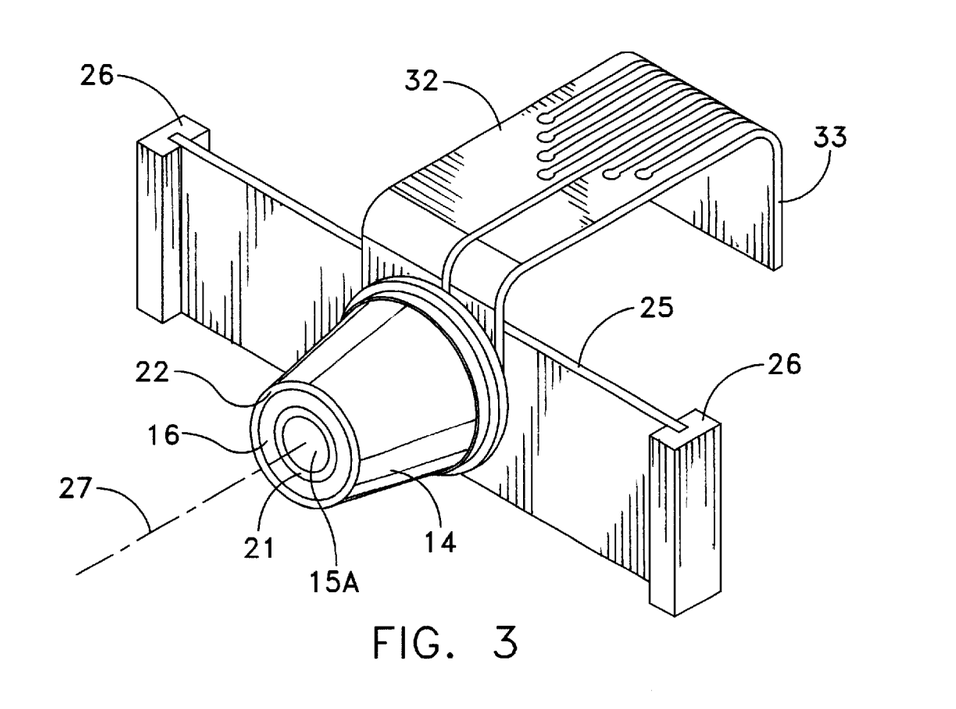
FIG. 3 is an alternate view of the structure shown in FIG. 2.

FIGS. 2 and 3 depict one embodiment of the sensor 14 and related support structures in greater detail. The sensor 14 mounts to a sensor support or beam 25 in the form of a planar sheet carried in end supports 26 that are shown schematically. The stiffness of the support 25 is selected so that over normal force ranges the support 25 deflects increasingly as force applied to the support increases as the sensor 14 is brought into contact with the skin or other substrate. Although not shown in the drawings, a stop can be incorporated to limit the total deflection of the support 25 and the sensor 14.

As shown more clearly in FIG. 3, deflecting the sensor 14 along an axis 27 enables piezoelectric transducers 30 and 31 mounted to the support 25 to produce a signal that is a function of the displacement of the board and hence the force applied to the board. Two such transducers provide a bipolar output signal in this specific embodiment.

Leads from these transducers 30 and 31 connect to a bus structure 32 that includes a connector section 33 for mating with a female connector mounted on a circuit board not shown. Other conductors on the connecting bus 32 will connect to the thermocouple 15 and to the electrode pair formed by the thermocouple can 15A and the concentric outer electrode 16, as shown more clearly in FIG. 2. Thus the bus 32 transfers signals representing instantaneous electrical characteristics, temperature and force values to circuitry attached through the connector section 33.

Figure 4:
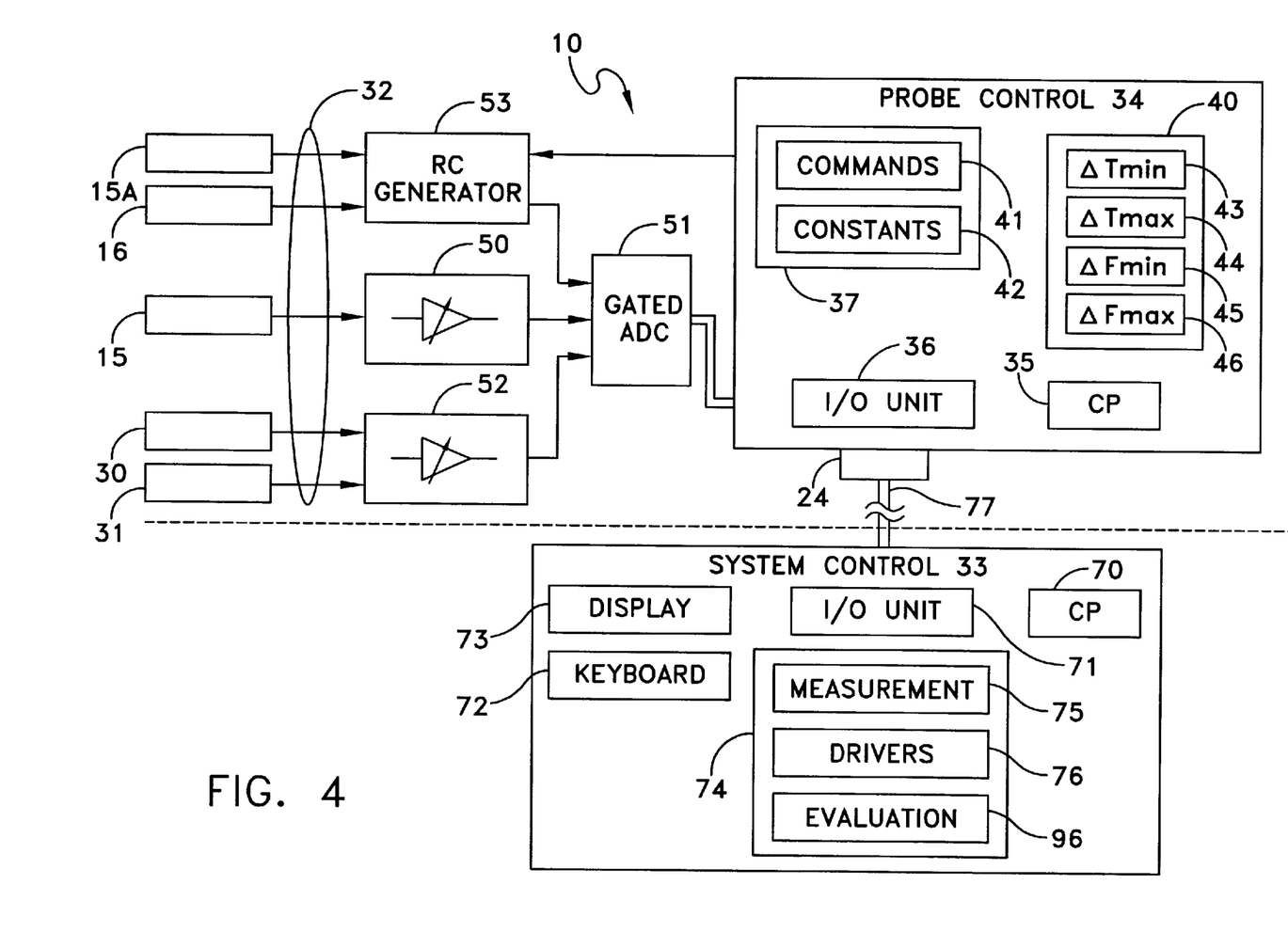
FIG. 4 is a schematic of circuitry for obtaining the normalized impedance measurements.

FIG. 4 depicts the probe 10 and an associated data processing system or system control 33 that provide a measurement of relative hydration in response to the signals from the electrodes 15A and 16, the thermocouple 15 and force transducers 30 and 31. In this particular embodiment the probe operates under the command of the system control 33. In a preferred embodiment the system control 33 can comprise any conventional CPU with an input/output interface such as an RS232 interface.

A probe control 34 that attaches to the connector 24 receives the signals and responds accordingly to each command. More specifically, the probe control 34 comprises a conventional micro-processor or other central processing system that includes a central processor (CP) 35, an I/O unit 36, a memory 37 and a second memory 40 typically implemented as in EPROM or other form of programmable read only memory. The probe control 34 produces the appropriate signals for indicating the instantaneous force, temperature and substrate characteristics in response to specific commands from the system control 33. The memory 37 includes modules or programs 41 for responding to such commands and, for purposes described later, a constants buffer 42. Of particular interest for this invention, the EPROM 40 includes four registers for storing particular constants. These includes a $\Delta T_{min}$ register 43, a $\Delta T_{max}$ register 44, $\Delta F_{min}$ register 45 and a $\Delta F_{max}$ register 46.

Still referring to FIG. 4, the temperature sensor 15 connects to a variable gain amplifier circuit 15 to produce an output signal in a predetermined voltage range that is applied to one input of a gated analog to digital converter (ADC) 51. Similarly, a variable gain amplifier 52 receives signals from the force transducers 30 and 31 for application to another input of the gated ADC 51.

Any number of circuits exist for providing a signal that indicates the moisture content. This probe uses an RC generator 53 that responds to an initiation signal from the probe control 34 to generate a signal having an RC time constant that is applied as another input to the gated ADC 51. In the system depicted in FIG. 4, a voltage pulse is applied to an RC circuit with the electrodes being in parallel with the RC circuit. The pulse has a fixed value and a duration exceeding a predetermined time. The initiation signal enables the RC generator to apply a reference signal to the gated ADC 51 and then to apply the capacitor voltage to the gated ADC. The gated ADC 51 operates at a high sampling frequency and is able to obtain voltage measurements over the rise time of the voltage of the capacitor. The result is a measurement of the complex impedance with a quantification of the capacitive reactance that is an indicator of substrate moisture.

As previously indicated, the probe 10 can be connected to the system control 33. Consequently it is important that the signals transferred to the system control 33 from different probes 10 reflect the same temperature and force readings. The probe control 34 with its registers 43 through 46, assures accurate and consistent readings from different probes by storing calibration information in the probe 10.

Figure 5:
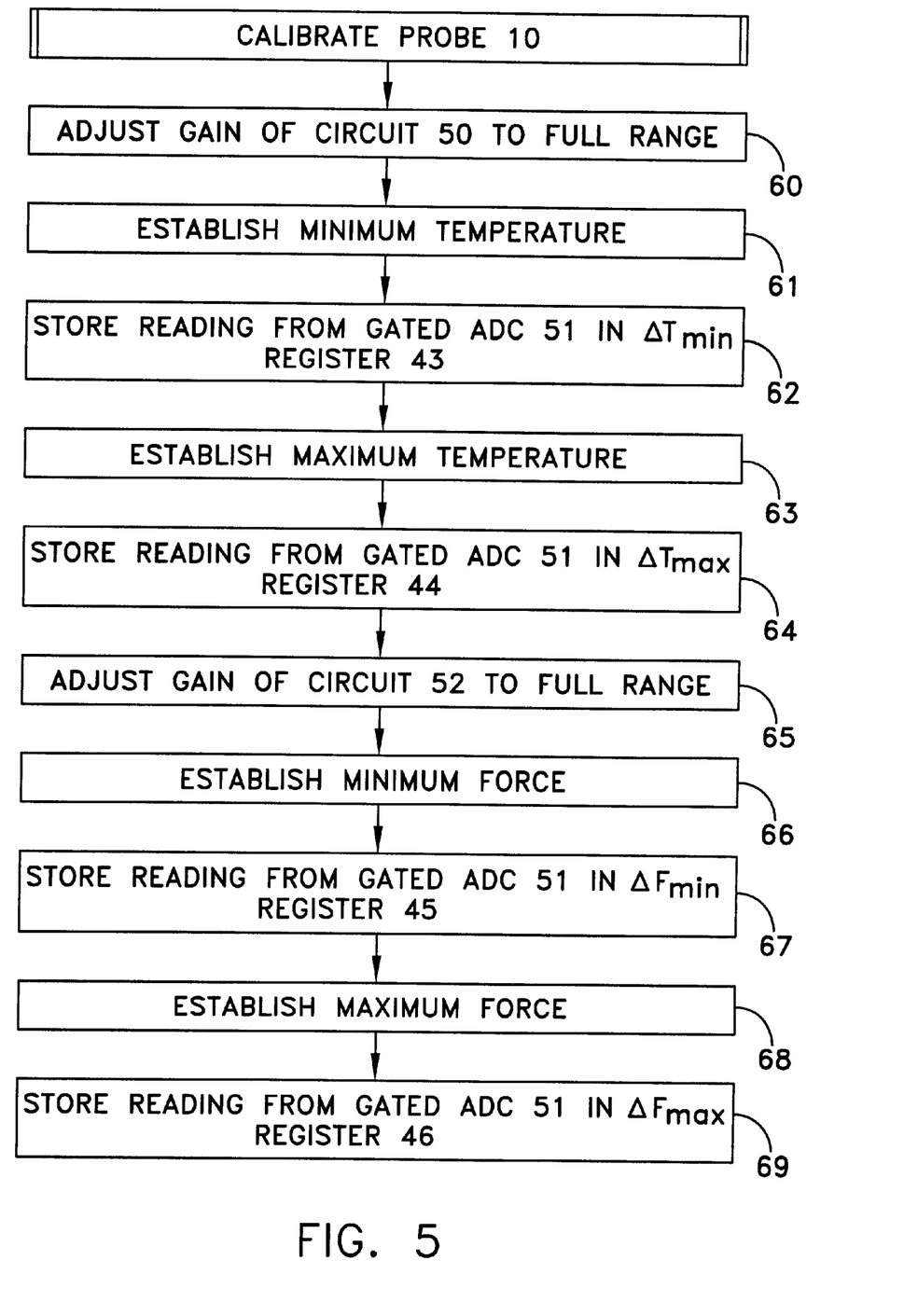
FIG. 5 is a flow diagram representing the steps for calibrating the sensor in FIG. 1.

FIG. 5 depicts a procedure for calibrating the probe 10 to achieve this consistency. This procedure occurs during the manufacturing process when the probe 10 is placed in an oven and the gain of the variable gain circuit 50 is adjusted over the operating ranges to provide a predetermined range of analog output signals or voltages from the variable gain amplifier 50 in step 60. When this iterative process has been completed, the oven will be held at the minimum temperature in accordance with step 61. Then the reading from the gated ADC 51 will be stored in a $\Delta T_{min}$ register 43 in step 62. After the temperature is raised to the maximum operating temperature, step 63 stores the reading from the gated ADC 51 in the $\Delta T_{max}$ register 44 in step 64.

A similar process is applied to the force transducers 30 and 31. A gain adjustment occurs in step 65. Then a minimum force is applied to the sensor in step 66 and the corresponding reading from the gated ADC 51 is stored in the $\Delta F_{min}$ register 45 in step 67. The value obtained from the gated ADC 51 at a maximum force obtained in step 68 is then stored in the $\Delta F_{max}$ register 46 in step 69.

In both cases, the range of the temperature and force preferably corresponds to a subset of the possible values from the gated ADC 51. For example, the gain and offsets might be selected so a minimum operating temperature produces a count of 5 and a maximum operating temperature a count of 246 on an eight-byte gated ADC output. As will now be apparent, a program in the memory 37 can, upon initialization cause the CP to calculate and store concordances between the measured counts and actual force and temperature or corresponding constants in a buffer such as the constants buffer 42. Thus output signals representing the force and temperature values of the system control 33 are accurate and repeatable from one probe to another.

During normal operation, the probe 10 connects to the system control 33 that includes a central processor 70, an I/O unit 71, an input keyboard or keypad 72 and a display 73. A memory 74 will contain, among other items, a measurement module or program 75 and various drivers 76. The measurement module 75 generates the commands for reading the force, i.e, a READ FORCE command, for reading temperature, i.e., a READ TEMPERATURE command, and for obtaining information from the RC generator 53, i.e. a READ CURVE command. These commands are communicated over a bus, such as a serial RS-232 bus 77 and the connector 24 to be received in the probe control 34.

Figure 6:
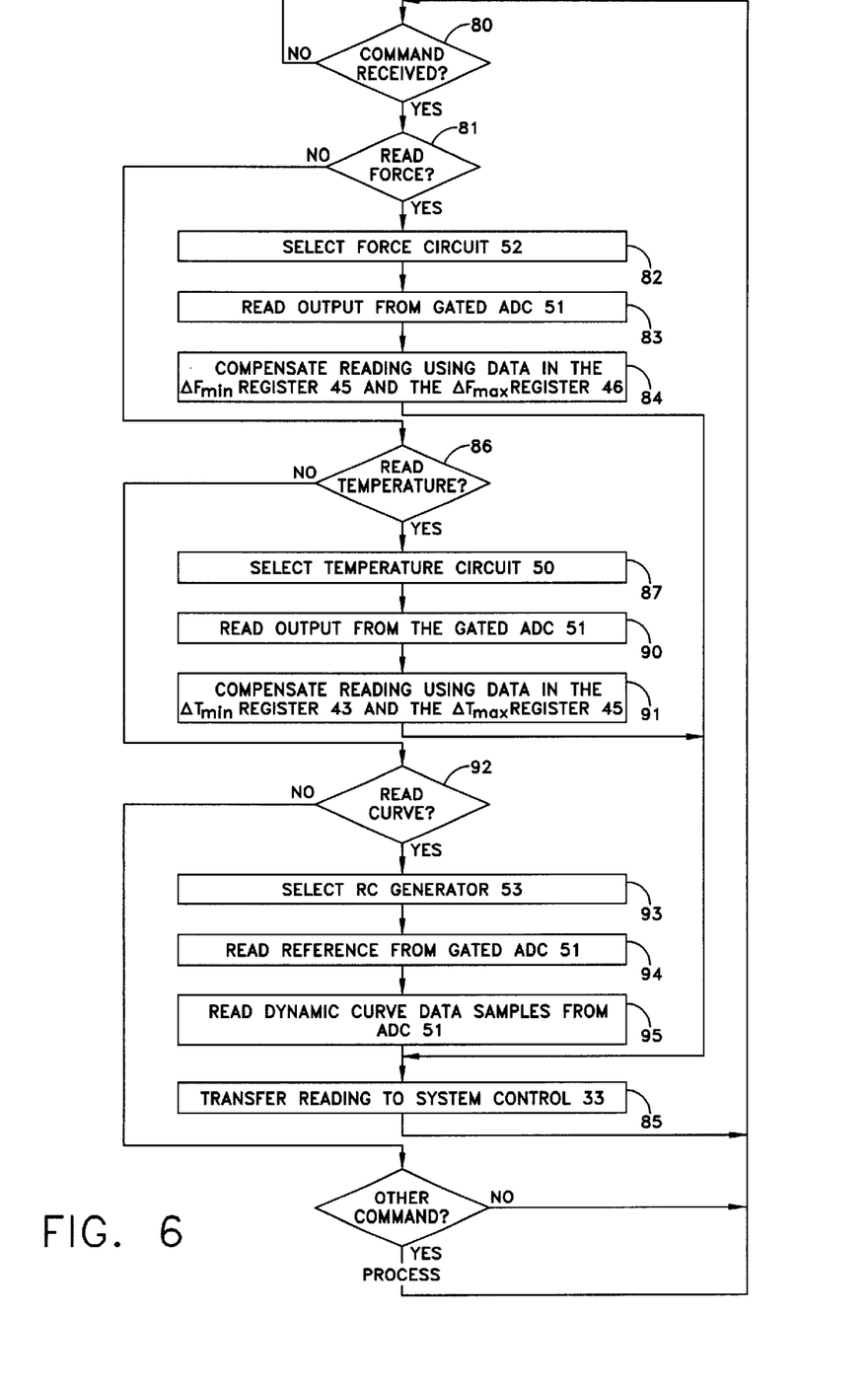
FIG. 6 is a flow diagram illustrating the steps for taking an impedance measurement.

In one particular embodiment, the central processor 35 operates under a control program to poll the I/O unit 36 to determine whether a command is received. This is shown in FIG. 6 at step 80. If a READ FORCE command is received, step 81 diverts control to step 82 that causes the I/O unit 36 to select and apply the signals from the amplifier 52 to the gated ADC 51 thereby to produce a number that the probe control reads at step 83. The control 34 then uses the $\Delta F_{min}$ and $\Delta F_{max}$ numbers, or information derived from those numbers and stored in the capacity buffer 42 or elsewhere during an initialization process, to provide a normalized force reading in step 84. Thereafter the corresponding data will transfer to the system control in step 85 and control of the central processor 35 then returns to await another command.

When a READ TEMPERATURE command is received, control passes through steps 80 and 81 to step 86 that then diverts control to step 87 whereupon the probe control 34 selects the temperature probe 15 as the input for the gated ADC 51. The probe control 34 then reads the output from the gated ADC 51 in step 90 and compensates that reading in step 91 in a fashion analogous to that in which the compensation of step 84 occurs.

The system again transfers control to step 85 so that the compensated output corresponding to the temperature transfers to the system control 33.

When a READ CURVE command is received by the probe control 34, the central processor 35 uses steps 80, 81 and 86 to transfer control to step 92 that diverts control to step 93. Step 93 selects the RC generator 53. Step 94 transfers a reference to the gated ADC 51 and that number is received and buffered by the probe control 34. This process also initiates the charging of a capacitor in the RC generator 53. The charging rate, in part, will depend upon the shunt impedance produced by the substrate across the electrodes 15A and 16. Step 95 takes a number of rapid samples of this charging voltage and the probe control buffers this information. When the process is complete step 95 transfers to step 85 wherein the reference and successive curve data samples are transferred back to the system control 33.

Thus it will be apparent that the measurement module 75 in FIG. 4 can obtain various readings from the probe 10 by issuing a sequence of commands such as the READ FORCE, READ TEMPERATURE and READ CURVE commands. An evaluation module 96 can then utilize the information for a number of functions and display information on the visual display 73, a printer or like device connected to the I/O unit 71 or LCD display 23 in the probe 10 shown in FIG. 1 the various readings that occur. With appropriate timing these can become data sets for purposes of evaluation.

Therefore there has been disclosed a probe 10 and a system control 33 that cooperate to obtain data concerning substrate hydration. The RC generator 53 and electrodes 15A and 16 coact to provide a measurement of relative substrate moisture. The amplifier 50 and thermocouple 15 provide a temperature at the sampling time, and an amplifier 52 and electrodes 30 and 31 provide an indication of the force with which the probe was applied to the skin during the measurement. This data can then be displayed for evaluation and further analysis for determining relative substrate hydration.

Figure 7:
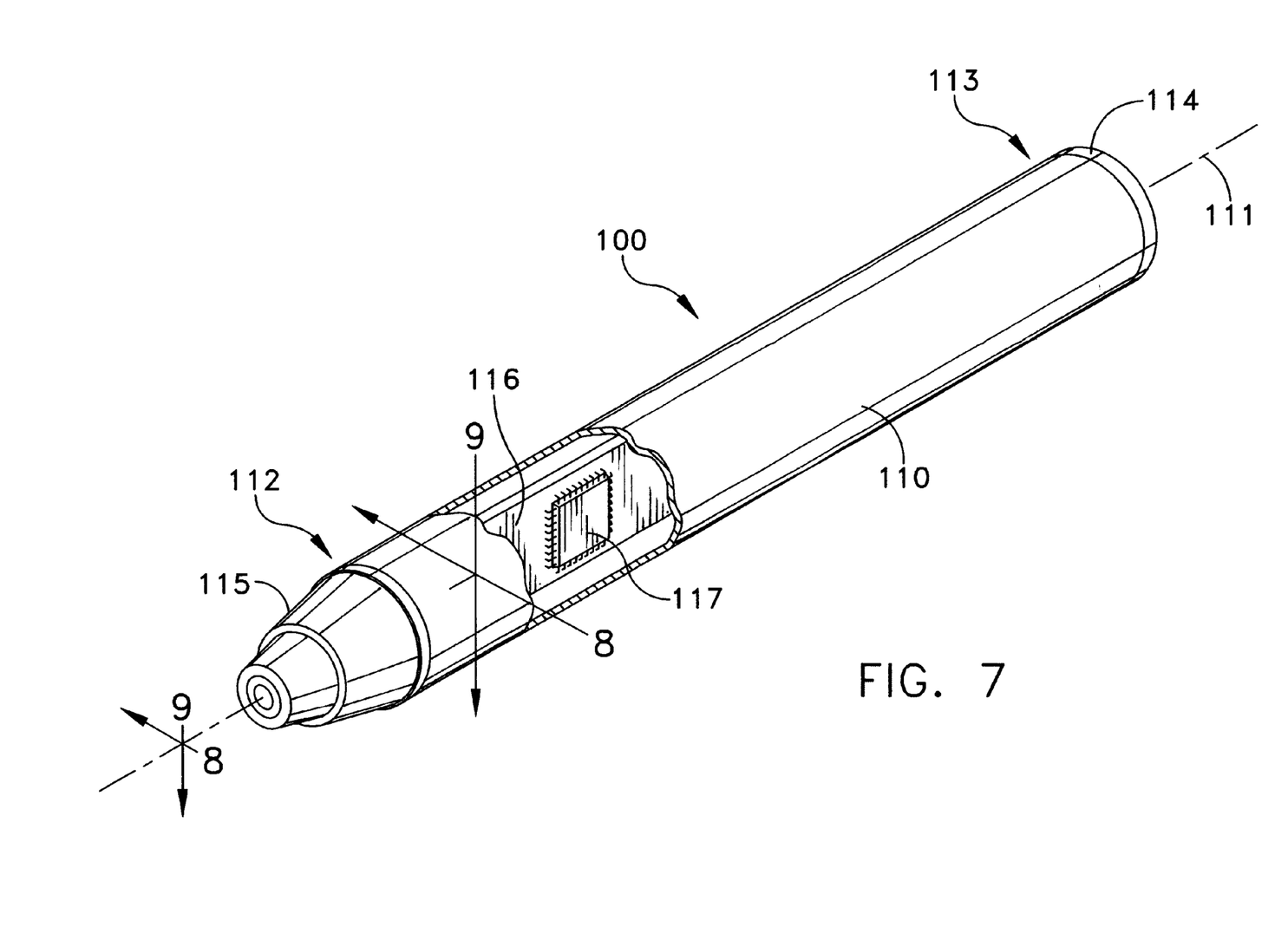
FIG. 7 is a view of an alternate, preferred embodiment of a sensor constructed in accordance with this invention.

FIG. 7 depicts a preferred embodiment of this invention that takes the form of a probe 100 that is a variation of the probe 10 in FIG. 1. The probe 100 contains a cylindrical housing 110 lying along an axis 111 between a first, distal end 112 and a second, proximal end 113. In the case of the probe 100 "distal" is meant to refer to the end that is most the proximate the patient. A connector 114 closes the proximal end 113 of the probe housing 110. The distal end 112 of the probe housing 110 carries a sensor body 115. In this particular embodiment the probe housing 110 also carries a printed circuit board 116 with a number of components represented by an integrated circuit 117. The components on the printed circuit board perform various functions. At a minimum they include the functions of the probe control 34 in FIG. 4. In other embodiments they may incorporate the functions of the system control 33 shown in FIG. 4. In certain applications, it may be desirable to include all the functions on the printed circuit board 116 and to operate the probe as a self-contained, battery operated measurement system. The end connector 114 could then be used as a convenient means for downloading data to a conventional computer system for storage and analysis.

Figure 8:
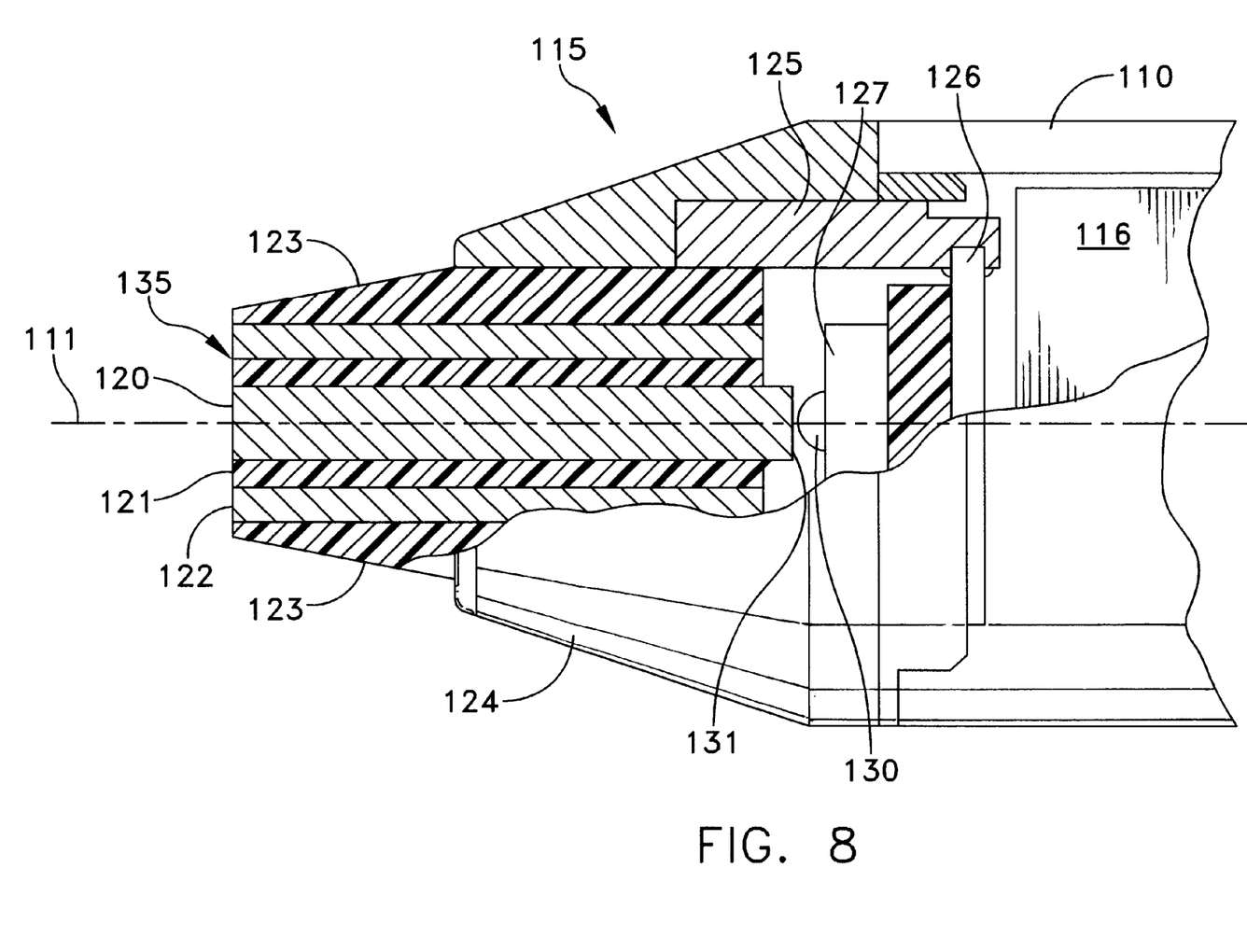
FIGS. 8 and 9 are views, partially in section, of a portion of the sensor taken along lines 8—8 and 9—9 in FIG. 7.
Figure 9:
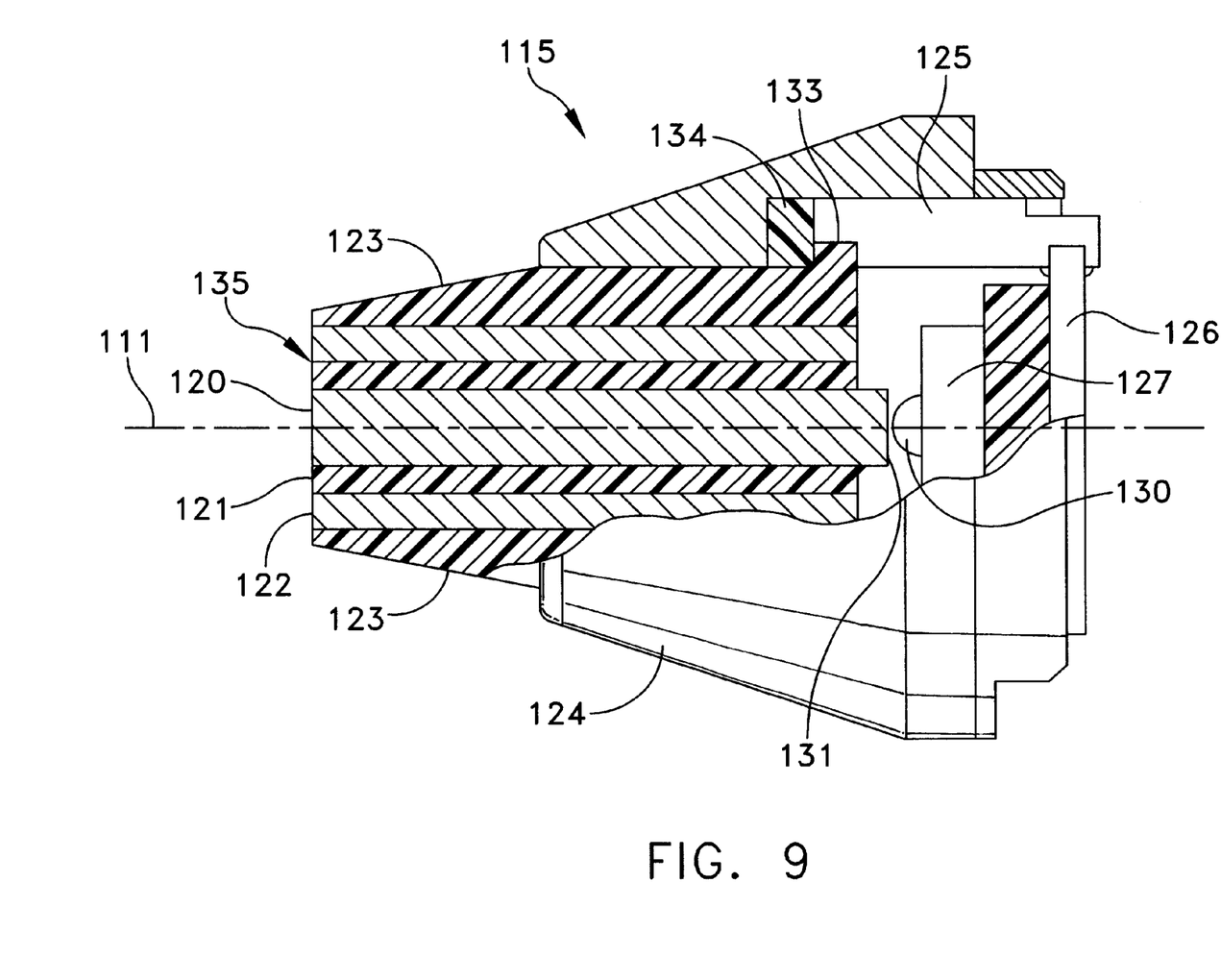

FIGS. 8 and 9 depict the detail of one sensor body 115 at the distal end 112 of the probe housing 110. The sensor body 115 includes a central conductor 120 that lies along an axis 111. An inner coaxial insulator 121 lies intermediate the central conductor 120 and an outer coaxial conductor 122 surrounds the inner insulator 121. In this specific embodiment, the central conductor 120 is cylindrical, and the coaxial conductor 122 has an annular form. An outer insulating body 123 is coaxial with this structure. In accordance with this invention the conductors 120 and 122 and the insulators 121 and 123 constitute a sub-assembly that fits within a housing 124 that, in turn, fits into the distal end 112 of the probe housing 110.

The housing 124 surrounds a standoff 125 that carries a rigid support 126 for a displacement type force sensor 127. The support 126 is transverse to the axis 111. The transducer 127 includes a plunger 130 that contacts a proximal end 131 of the center conductor 120 and that transfers any force to internal measuring components within the transducer 127 that deflect under load. When the sensor body 115 is assembled, the sub-assembly comprising the conductors 120 and 122 and the insulators 121 and 123 is slip fit into the housing 124 such that the sub-assembly can be displaced incrementally along the axis 111. During manufacture, this sub-assembly is shifted fully to the left until a flange 133 formed on a portion of the outer insulator 123 engages a projection 134 on the standoff 125 that defines a distal-most position of the subassembly, as shown in FIG. 9. Next the position of the support 126 in the standoff 125 is adjusted until the plunger 130 just engages the end 131 of the central conductor 120. Then the support 126 is fixed to the standoff 125, as by soldering or the like. In use, when the probe 100 in FIG. 7 is applied to a substrate, the distal end 135 of the sensor body 115 contacts the substrate. As force is applied by urging the probe housing 110 distally, to the left in FIG. 7, the sub-assembly including conductors 120 and 122 and insulators 121 and 123 tends to shift proximally thereby to increase the force on the plunger 130 whereupon the transducer 127 generates a force signal that varies with the applied force. When the probe 100 is removed from the substrate, the internal components of the transducer, as known, relax and return the sub-assembly to its original position.

FIG. 8 does not depict the connections of electrodes 120 and 122 to, or any conductive paths for conveying force signals to, circuitry on the printed circuit board 116. Such connections are well within the capabilities of persons of ordinary skill in the art.

Any number of different mechanical configurations could be devised to provide this force measuring function. The structure in FIGS. 8 and 9 could also be constructed to accommodate a temperature sensor in the same fashion as is described with FIGS. 1 and 2.

Figure 10:
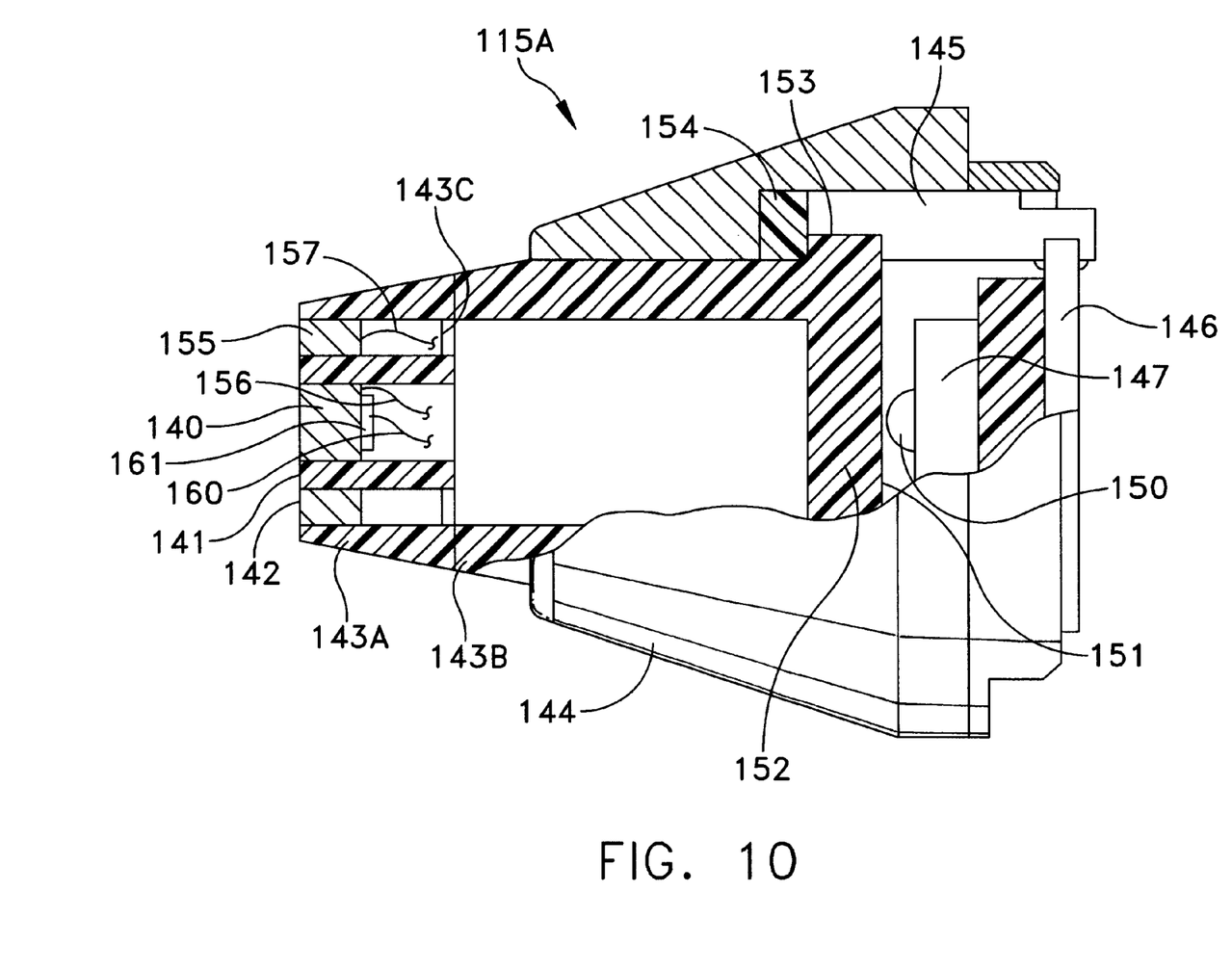
FIG. 10 is a view, partially in section, of an alternate structure for the sensor shown in FIGS. 8 and 9.

If the conductors 120 and 122 are formed of a highly conductive material, they can act as a heat sink that artificially lowers the apparent temperature of the substrate and introduce errors into any temperature readings. FIG. 10 depicts an alternative structure that minimizes temperature errors. A sensor body 115A has the same general configuration as the sensor body 115 in FIGS. 8 and 9. However, the central conductor 140 and the annular conductor 142 are constituted by a conductive pad and ring, respectively, that lie only at the distal end of an annular insulator 141. All these lie inside an outer insulator that comprises two axially positioned, contiguous sections 143A and 143B and in a cover 144. The distal section 143A includes inwardly extending, angularly spaced radial spokes or arms 143C that support the inner insulator 141.

The sensor body 115A in FIG. 9 also includes a standoff 145 that carries a transverse support 146 for a displacement type force transducer 147 with a plunger 150. In this particular example, however, the annular insulator portion 143B provides as surface 151 for contacting the plunger 150 by means of a closed end 152. The closed end 152 also forms radially extending, angularly spaced shoulders, such a shoulder 153, that are partially coextensive with the circumference of the outer insulator portion 143B, like the shoulder 133 in FIG. 9. Thus, as a force is applied to an end 155 of the sensor sub-assembly, the sub-assembly including the conductors 140 and 142 and the insulators 141, 143A and 143B, tend to shift proximally thereby to transfer the force through the plunger 150 to the transducer 147 to produce a force signal.

FIG. 10 depicts conductors 156 and 157 attached to the central and annular conductors 140 and 142 respectively and a conductor 160 attached to a thermistor 161. The conductors 156, 157 and 160 are merely shown as being representative of connections that would made of any various means available to those of ordinary skill in the art to provide the corresponding signals to circuitry on the printed circuit board 115 shown in FIGS. 7 and 8.

With this structure the central conductor 140 and the outer conductor 142 continue to function as electrodes for obtaining substrate impedance measurements. However, the reduced axial length of each minimizes any heat sink effect. Consequently the thermistor 161 can provide more accurate temperature readings related to the substrate temperature at the site being monitored.

Thus in accordance with this invention there have been disclosed different embodiments of a measurement system for relative substrate hydration that can produce indications of the moisture content of the substrate for a number of different applications. Each is characterized by having an elongated probe housing with a sensor body mounted at a distal end that has first and second electrodes for contacting the substrate at a site for which a relative hydration measurement is desired. Each acts as an input to an electrical impedance measurement circuit. Each includes a force sensor in the probe housing for generating a signal representing the force exerted by the sensor body on the substrate, as an example of an environmental factor. In each a signal processor can use polling or other techniques to obtain these signals. FIGS. 3 and 4 further depict specific circuitry that can be contained either completely or partially within the probe housing to obtain various values.

It will be apparent, that a number of variations can be made to the specifically disclosed embodiment without departing from the true spirit and scope of this invention. For example, specific detailed sensor body structures have been shown. Other structures could be substituted using different force transducers and temperature sensors. The circuitry on a printed circuit board, such as the printed circuit board 116 shown in FIG. 7, can contain some or all of the electronics shown in FIGS. 3 and 4 or even contain all the circuitry necessary for identifying patients and storing information for subsequent downloading to an external data processing system.

Therefore, it is the intent of the appended claims to cover all such variations and modifications as come within the true spirit and scope of this invention.

What is claimed as new and desired to be secured by Letters Patent of the United States is:

1. A system for measuring the relative hydration of a substrate comprising:

A) a probe having first and second electrodes for contacting the substrate at a site for which a measurement is desired, B) an electrical impedance measurement circuit for periodically generating a value representing substrate impedance between the first and second electrodes, C) an environmental factor measurement circuit for periodically generating a value representing a substrate environmental factor associated with the impedance measurement, and D) a substrate hydration calculator for combining the impedance and environmental factor signals to generate an output representing the relative hydration of the substrate.

2. A system as recited in claim 1 wherein the environmental factor is substrate temperature and said environmental factor measuring circuit includes a temperature sensor in said probe for generating a signal representing substrate temperature at the site.

3. A system as recited in claim 1 wherein the environmental factor is a force with which said probe is applied to the substrate and said environmental factor measuring circuit includes a force sensor for measuring force applied to one of said electrodes.

4. A system as recited in claim 3 additionally comprising a temperature sensor in said probe for generating a signal representing substrate temperature at the site.

5. A system for measuring the relative hydration of a substrate including a measurement probe and a data processing system wherein said measurement probe comprises:

A) an elongated probe housing,

B) a sensor body mounted at one end of said probe housing with first and second concentric electrodes for contacting the substrate at a site for which a measurement is desired, C) an electrical impedance measurement circuit in said probe housing for generating an impedance signal representing substrate impedance between the first and second electrodes, D) a force sensor in said probe housing for generating a signal representing a force exerted by one of said electrodes on the substrate, E) a signal processor in said probe housing for polling said electrical impedance measurement circuit and said force sensor thereby to generate processed impedance and force measurement signals, and F) a connector at the other end of said probe housing for enabling communications of the processed impedance and force measurement signals to said data processing system from said signal processor whereby the data processing system combines the processed impedance and force measurement signals to produce a measurement of relative hydration.

6. A system as recited in claim 5 wherein said probe housing lies along an axis, said first electrode comprises a central conductor lying on the axis and said second electrode comprises a conductor coaxial with and spaced from said central conductor, said probe additionally including an insulatory between said central and coaxial conductors.

7. A system as recited in claim 6 wherein said sensor body extends between a first end that contacts the substrate and a second end proximate said probe housing, said force sensor comprising:

i) a support attached at the second end of said sensor body transverse to the axis, and ii) a displacement force transducer on said support and contacting said sensor body whereby any force applied to the first end of said sensor body is transmitted through said coaxial conductor to said force transducer.

8. A system as recited in claim 7 wherein said probe is adapted to undergo a specified range of forces having first and second ends and wherein said signal processor includes first and second storage registers for the signal values from said force transducer when the force applied to said coaxial conductor is at the first and second ends of the force range, respectively.

9. A system as recited in claim 7 additionally comprising a temperature sensor in said sensor body to sense substrate temperature proximate the site at which said electrodes contact the substrate, said signal processor additionally including a circuit for generating a processed temperature signal for transfer to the data processing system.

10. A system as recited in claim 9 wherein said probe is adapted to operate under a specified range of substrate temperatures having first and second ends and wherein said signal processor includes third and fourth storage registers for the signal values from said temperature sensor when the temperature applied to said temperature sensor is at the first and second ends of the substrate temperature range, respectively.

11. A system as recited in claim 9 wherein said signal processor provides outputs for each of the impedance, force and temperature readings and wherein said data processing system includes means for requesting the transfer of each of the readings.

12. A system as recited in claim 9 wherein said signal processor provides outputs for each of the impedance, force and temperature readings and wherein said data processing system includes means for requesting the transfer of each of the readings on an iterative basis.

13. A system for measuring relative hydration of a substrate including a measurement probe and a data processing system wherein said measurement probe comprises:

A) an elongated probe housing extending between first and second ends,

B) a sensor body mounted at the first end of said probe housing with first and second concentric electrodes for contacting the substrate at a site for which a moisture measurement is desired, C) an electrical impedance measurement circuit in said probe housing for generating an impedance signal representing substrate impedance between the first and second electrodes, D) a temperature sensor in said probe housing for generating a signal representing substrate temperature contacting said electrodes, E) a signal processor in said probe housing for polling said electrical impedance measurement circuit and said temperature sensor thereby to generate processed impedance and temperature measurement signals, and F) a connector at the second end of said probe housing for enabling communications between said data processing system and said signal processor whereby the data processing system combines the processed impedance and temperature signals to produce a measurement of relative hydration.

14. A system as recited in claim 13 wherein probe housing lies along an axis, said first electrode comprises a central conductor lying on the axis and said second electrode comprises a conductor coaxial with and spaced from said central conductor, said probe additionally including an insulator between said central and coaxial conductors.

15. A system as recited in claim 14 wherein said probe is adapted to operate under a specified range of substrate temperatures having first and second ends and wherein said signal processor includes first and second storage registers for the signal values from said temperature sensor when the temperature applied to said temperature sensor is at the first and second ends of the temperature range, respectively.

16. A system as recited in claim 15 wherein said signal processor provides outputs for each of the impedance and temperature readings and wherein said data processing system includes means for requesting the transfer of each of the readings.

17. A method for measuring relative hydration of a substrate comprising the steps of:

A) measuring electrical characteristics of the substrate between electrodes contacting the substrate, B) measuring an environmental factor of the substrate concurrently with said measurement of electrical characteristics, and C) utilizing the measurements for said electrical characteristics and environmental factor measurements for obtaining a substrate impedance value that represents relative hydration of the substrate.

18. A method as recited in claim 1 wherein said environmental factor is substrate temperature and said environmental factor measuring includes measuring the temperature of the substrate at the site of said electrical characteristic measurement.

19. A method as recited in claim 1 wherein said substrate electrical characteristics measurement includes applying an electrical impedance sensor to a site of the substrate and said environmental factor is the force with which the impedance sensor is applied to the substrate, said environmental factor measuring including measuring the force on the impedance sensor at the site of the electrical impedance sensor measurement.

20. A method as recited in claim 1 wherein said environmental factor measuring includes measuring the temperature of the substrate at the site of the electrical impedance characteristics measurement.

21. A method as recited in claim 1 wherein said electrical characteristic measuring step includes:

i) applying a probe with first and second electrodes to a site of the substrate, and ii) iteratively measuring the impedance of the substrate between the electrodes at the site.

22. A method as recited in claim 21 wherein said environmental factor is the substrate temperature and said environmental factor measuring includes iteratively measuring the temperature of the substrate at the site of said electrical impedance measurement concurrently with said iterative impedance measurement.

23. A method as recited in claim 21 wherein said environmental factor is a force with which the probe is applied to the site and said environmental factor measuring includes iteratively measuring the force of the probe at the site of the electrical impedance measurement.

24. A method as recited in claim 23 additionally comprising the step of iteratively measuring substrate temperature at the site of the electrical impedance measurement.

* * * * *

UNITED STATES PATENT AND TRADEMARK OFFICE
CERTIFICATE OF CORRECTION

PATENT NO. : 6,370,426 B1
DATED : April 9, 2002
INVENTOR(S) : Michael J.E. Campbell et al.

It is certified that error appears in the above-identified patent and that said Letters Patent is hereby corrected as shown below:

Column 8,
Line 23, delete "115" and insert -- 116 --

Column 11,
Lines 25 and 30, delete "1" and insert -- 17 --

Column 12,
Lines 6 and 10, delete "1" and insert -- 17 --

Signed and Sealed this

Tenth Day of August, 2004

JON W. DUDAS
*Acting Director of the United States Patent and Trademark Office*